US00PP26901P2

(12) United States Plant Patent
Yakligian

(10) Patent No.: US PP26,901 P2
(45) Date of Patent: Jul. 5, 2016

(54) PEACH TREE NAMED '2343 JAY DAY'

(50) Latin Name: *Prunus persica*
Varietal Denomination: 2343 Jay Day

(71) Applicant: James Yakligian, Sanger, CA (US)

(72) Inventor: James Yakligian, Sanger, CA (US)

( * ) Notice: Subject to any disclaimer, the term of this patent is extended or adjusted under 35 U.S.C. 154(b) by 0 days.

(21) Appl. No.: 14/757,030

(22) Filed: Nov. 9, 2015

(51) Int. Cl.
*A01H 5/08* (2006.01)

(52) U.S. Cl.
USPC ..... Plt./197

(58) Field of Classification Search
USPC ..... Plt./197
See application file for complete search history.

(56) References Cited

U.S. PATENT DOCUMENTS

PP15,496 P2 1/2005 Slaughter et al.

OTHER PUBLICATIONS

Upov International Union for the Protection of New Varieties of Plants UPOV?INF/12/4 Nov. 1, 2012, 16 pp.*

* cited by examiner

*Primary Examiner* — June Hwu
(74) *Attorney, Agent, or Firm* — Mark D. Miller

(57) ABSTRACT

A new and distinct variety of peach tree which it is distinguished by producing late ripening fruit which are mature approximately October 15-31 in a normal year.

5 Drawing Sheets

BACKGROUND OF THE NEW VARIETY

The present invention refers to a new variety of peach tree which will hereinafter be denominated as the '2343 Jay Day peach tree which produces clingstone fruit which are mature for commercial harvesting and shipment approximately October 15-31 in a normal growing year in the San Joaquin Valley of Central California as a late fresh market peach with a good red blush coloration.

In the development of new commercial varieties of fruit specific characteristics places a premium on those varieties, which are early or late maturing, in the growing season. However, many such varieties have small size, lack of flavor, or coloration. In some instances there are other undesirable characteristics that decrease the commercial success. In order for a fruit to be a commercial success it must possess those characteristics of good size, good color, and good flavor. At the same time the date of maturity must be separate or different than other similar fruit. This new invention meets all of the aforementioned criteria and therefore is of commercial appeal to the consumer.

ORIGIN AND ASEXUAL REPRODUCTION OF THE NEW VARIETY

The present variety of peach tree was discovered by the inventor growing next to a swine pen adjacent to his orchard of 'Calara' peach trees (U.S. Plant Pat. No. 15,496) which is located near Sanger, Calif. The inventor discovered it as a seedling in 2012 and observed it for three years. The parentage is unknown. The new variety was asexually reproduced by the inventor in 2015 by bud grafting of trees onto 'Nemaguard' (unpatented) rootstock in the adjacent orchard of origin. The inventor has carefully examined the asexually reproduced trees which appear to be highly similar to the 'Calara', but which are not expected to first bear fruit until October 2016.

SUMMARY OF THE NEW VARIETY

The subject '2343 Jay Day' tree is characterized by producing a large clingstone fruit which has good red blush coloration and is ripe for commercial harvesting and shipment approximately October 15-October 31 in the San Joaquin Valley of Central California. The new variety is similar to 'Calara' peach tree (U.S. Plant Pat. No. 15,496), but from which is distinguishable in that the fruit is similar and size and appearance but ripens many weeks later than the fruit of 'Calara' peach tree. The fruit of this new variety possesses a very good flavor as well as aroma which is greatly acceptable for a late ripening variety.

BRIEF DESCRIPTION OF THE DRAWING

The accompanying drawings are color photographs showing fruit and foliage of the new variety.

DETAILED DESCRIPTION

Figure 1:
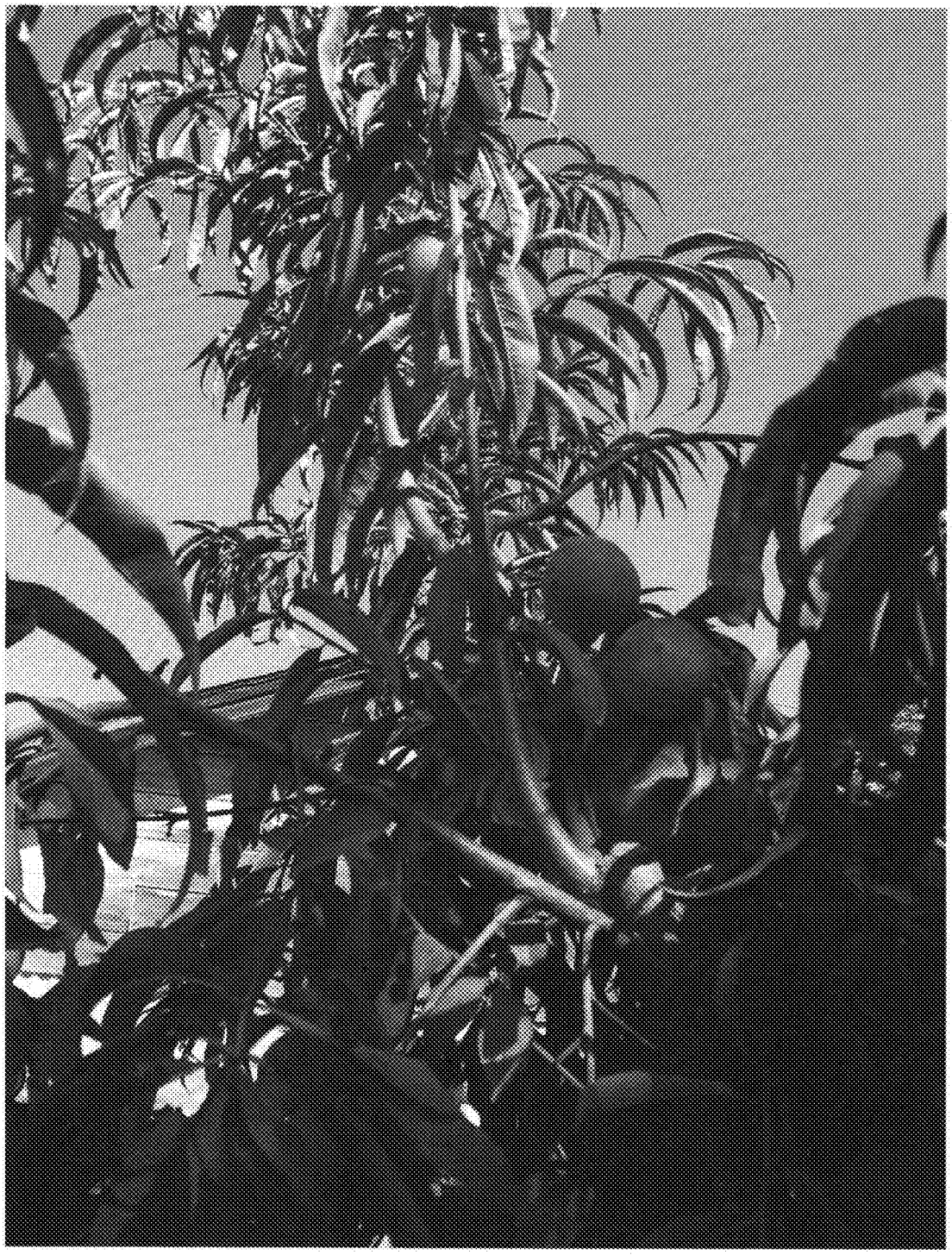
FIG. 1 shows branches, leaves and fruit of a tree of the new variety in situ.
Figure 2:
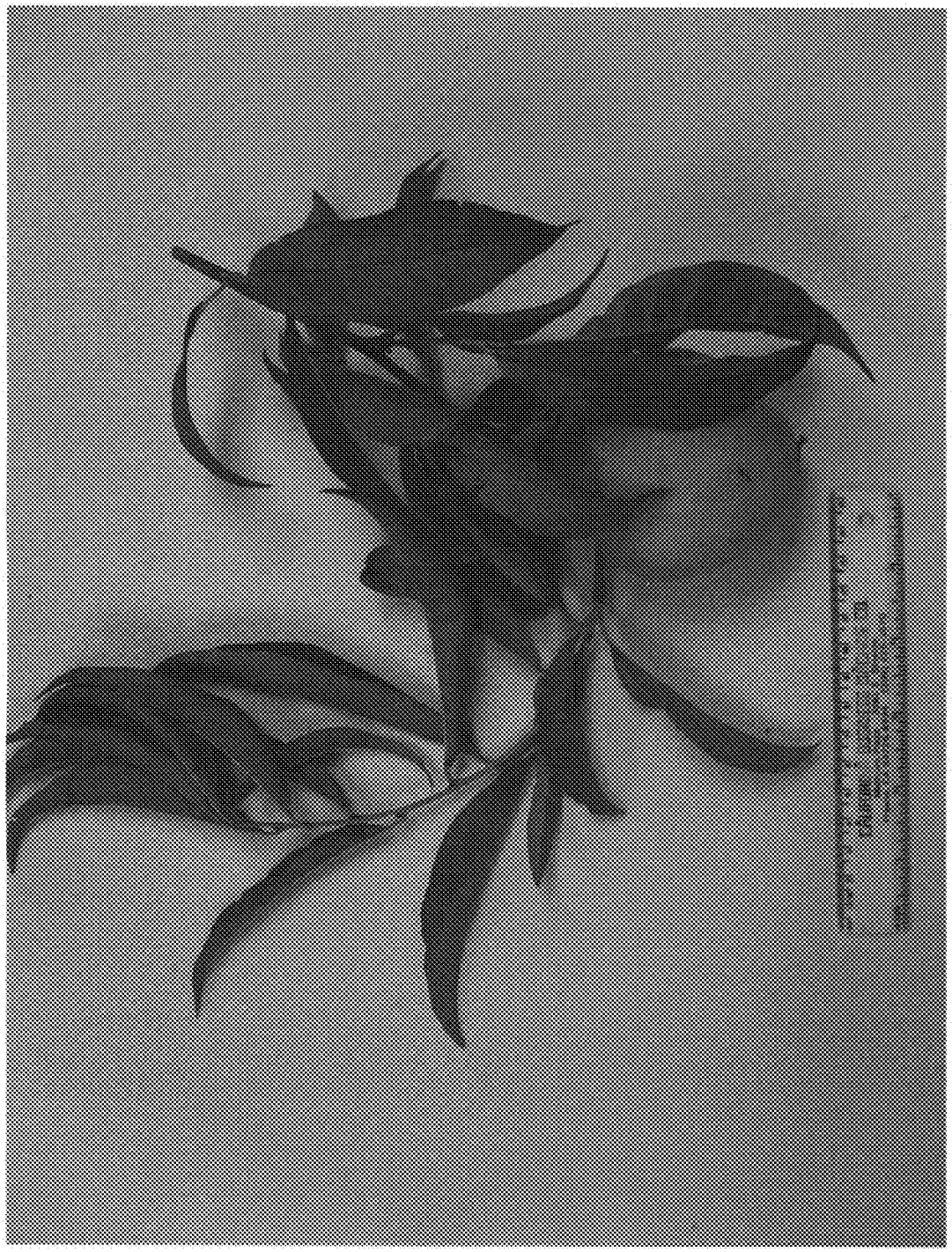
FIG. 2 shows a close up of leaves and branches of the new variety.
Figure 3:
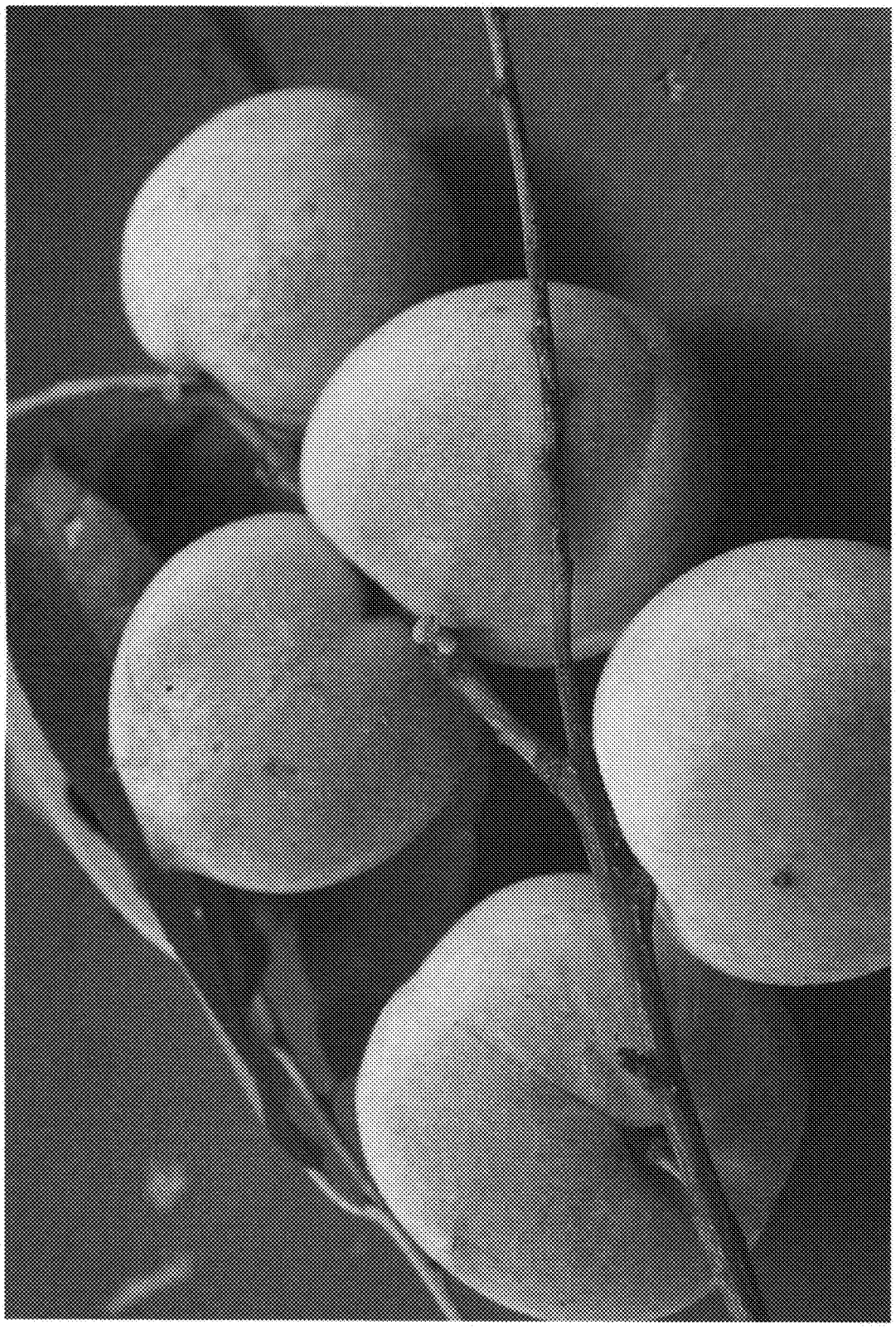
FIG. 3 shows whole uncut fruit of the new variety.
Figure 4:
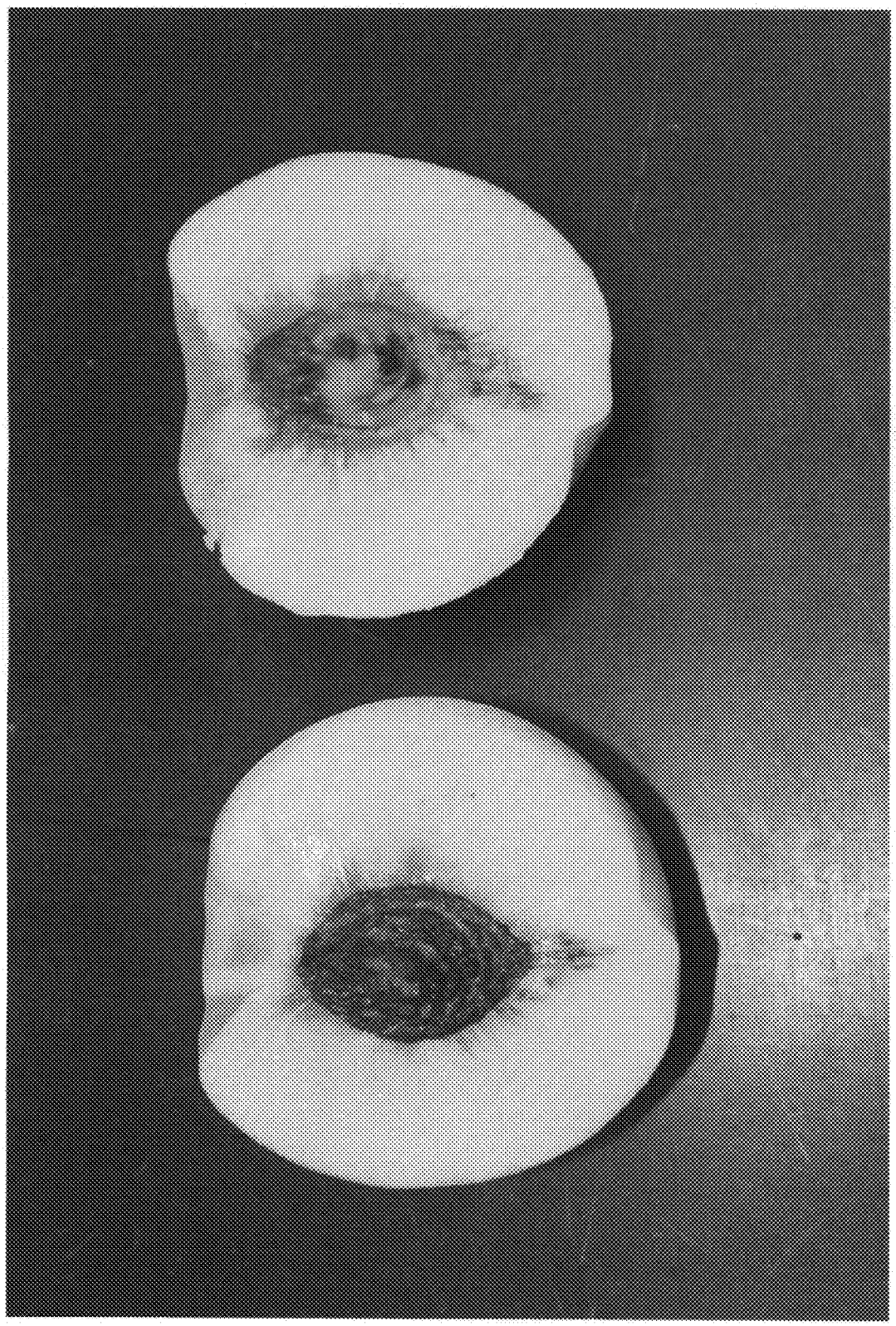
FIG. 4 shows cut fruit of the new variety showing the pit, stone and flesh.
Figure 5:
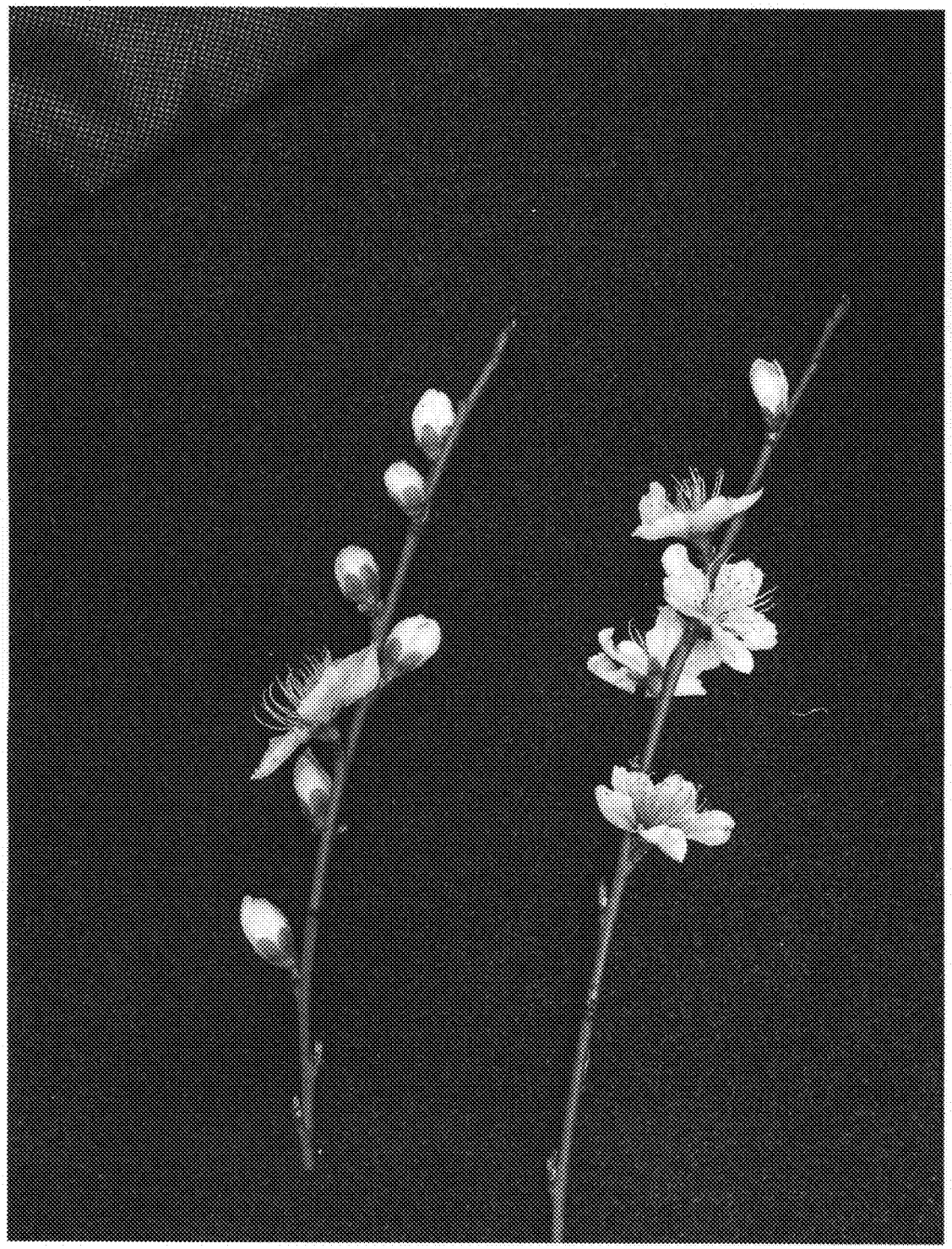
FIG. 5 shows branches of the new variety with flowers and buds.

Referring more specifically to the pomological description of this new and distinct variety of peach tree, the following has been observed under the ecological conditions prevailing in the location of origin which is near Sanger, Calif. in the San Joaquin Valley of Central California. All major color code designations are by reference to the Dictionary of Color by Maerz & Paul, First Edition 1930. Common color names are also occasionally employed.

TREE

Size: Tree is similar in size and growth habit to 'Calara' U.S. Plant Pat. No. 15,496. 10 ft×10 ft—medium size for peaches.

Vigor: Moderate at $4^{th}$ year of growth.

Figure (form): Upright and spreading with open vase system of training. Productivity is very good for tree in fourth year of growth. Regularity of bearing appears to be regular (i.e., every year, not in alternate years).

Trunk size: Medium (diameter 9", 10" above soil level)—moderately rough.

*Color*.—Olive drab, 15-J-1 to 15-J-12.

*Lenticels*.—Oval form, medium. Length: from 2-10 mm. Color: tan, 11-G-4. Number: many.

Branches:

*Size*.—Medium.

*Surface texture*.—Slightly rough. a. Mature — Slightly Rough. b. Immature — Smooth.

*Color code* (*one year or older*).—Bronze-umber, 15-J-11.

*Color code* (*immature*).—Light green, 18-G-6. Three to four scaffold with lateral branches, at this stage of growth, being develop fruit wood and allow maximum sunlight for fruit colors. Diameter of scaffold branches taken at about two feet above soil level is 3-4 inches in circumference.

LEAVES

Size: Medium to large.

Length: 57-174 mm.

Width: 30-45 mm.

Shape: Lanceolate, leaf tip acuminate.

Texture: Smooth.

Color code:

*Upwardly disposed surface* (*upper side*).—Light green, 25-A-10.

*Downwardly disposed surface* (*underside*).—Pale green, 18-H-6.

Marginal form: Crenate, slightly undulate in larger leaves.

Leaf vein:

*Color code*.—Very pale green, 18-H-4.

*Thickness*.—0.5-1.5 mm.

Glandular characteristics: Reniform—alternate.

*Color*.—Cocoa turtle apache +, sahara –, 7-E-12.

*Size*.—2 mm.

*Number*.—2-4.

Petiole:

*Size*.—Medium.

*Length*.—From 7-10 mm.

*Diameter*.—From 1.5-2 mm.

*Color code*.—Pale yellow-green, 18-L-4.

Leaf bud burst occurs during the third to fourth week in February in a normal year. The stipule length at approximately one week after bud burst averaged 0.9 cm in length (0.8-1 cm) on the most mature leaves.

FLOWERS

Flower buds: Hardy under typical central San Joaquin Valley climate condition.

*Size*.—Dormant buds of average size.

*Length*.—From 8-16 mm.

*Form*.—Ellipsoidal and slightly appressed to the bearing wood.

Bud scales:

*Color*.—Chianti Antique Ruby+ (6-L-6) and pubescent on surface.

Generally: Showy type.

Date of bloom: 100% bloom as of March 1, later than parent 'Calara'.

Size: Generally medium to large.

Diameter: When fully expanded 25-30 mm (0.98 in-1.18 in).

Bloom quality: Abundant.

Fragrance: Slight—typical peach.

Petals:

*Size*.—Medium to large. Length: 15 mm (0.59 inch) to 18 mm (0.71 inch). Width: 10 mm (0.39 inch) to 13 mm (0.51 inch).

*Form*.—Broadly ovate.

*Number*.—Five.

*Color*.—Pink (41-K-1) to very very light pink (41-B-1) at apex.

*Petal claws*.—Broadly truncate. Width: 1 mm (0.039 inch). Length: 1.5 mm (0.059 inch).

*Petal margins*.—Moderately undulated with somewhat rounded margins.

*Flower pedicel*.—Very short 3-4 mm (0.12 inch-0.16 inch). Color: green (21-H-11). Surface: glabrous. Diameter: 1-2 mm (0.039 inch-0.079 inch).

Sepals:

*Surface*.—Pubescent.

*Size*.—Medium to large.

*Form*.—Broadly ovate.

*Color*.—Maroon (55-H-7) to green (21-K-9) with same color maroon spots/flecks.

*Number*.—Five.

Calyx:

*Color*.—Bronze (15-E-10) at base and maroon (55-H-7) near base of sepals.

Anthers:

*Size*.—Average.

*Color*.—Azalea (4-J-3).

*Position of stigma*.—Level in relation to the anthers.

Stamen: 8-15 mm (0.31 inch-0.59 inch).

*Number*.—25-30.

*Position*.—Level in relation to the petals.

Pollen is present: Color: narcissus (10-K-4).

Filament: Color: white (17-A-1) to light pink (51-F-1).

Pistil:

*Length*.—Average 20 mm (0.79 inch).

*Number*.—One.

*Color*.—Light green (17-J-7).

*Surface*.—Pubescent.

*Pubescence present in ovaries*.—Ovary densely covered with unbranched, multicellular trichomes, from 0.5 to 2 mm in length.

FRUIT

Date of maturity: October 15-31 in a normal year.
Size:
*Diameter axial plane*.—From 61-78 mm.
*Transverse in suture plane*.—From 58-79 mm.
*Transverse at rt. angle to suture plane*.—From 58-80 mm.
Form: Uniform.
*Symmetrical or asymmetrical*.—Shape of fruit is slightly asymmetrical.
Suture: Shallow but with distinct pumpkin orange (10-H-11) coloration from base to apex.
Ventral surface: Uneven.
Stem cavity:
*Width*.—From 6-8 mm.
*Depth*.—From 12-19 mm.
*Length*.—From 9-13 mm.
*Shape*.—Oval.
Stem: Short.
*Diameter*.—From 2-3 mm.
Apex: Slightly Rounded.
Pistil point: Oblique.
Skin: Thickness normal for peach, light pubescence.
Sweetness: Medium/high.
Acidity: Medium.
Texture: Firm.
Tendency: None observed.
Color code:
*Blush color*.—Deep pinkish orange, 9-H-9 to 9-H-12.
*Ground color*.—Varies over 50% at axis, from yellow to orange, 9-J-1 to 9-J-8.
*Flesh color*.—Bright yellow, 9-L-1.
*Color at surface of pit cavity*.—Sungod streaks, 2-H-12.
*Color of pit well*.—Orange with reddish streaks, 2-A-11 to 3-L-11.
Juice production: Moderate.
Flavor: Very good to excellent.
Aroma: Good.
Fibers:
*Number*.—Few.
*Texture*.—Firm.
Ripening: Even.
Eating quality: Very good to excellent.
Stone:
*Attachment*.—Clingstone.
*Fibers*.—Numerous, Short, slightly thick.
*Size*.—Medium. Length: from 33-38 mm. Width: from 22-25 mm. Diameter: from 16-18 mm.
Form: Ovate.
Apex: Sharply acute.
Color code, when dry: Light orange-tan to dark reddish brown, 3-B-11 and 8-C-6.
Base: Slightly rounded.
Sides: Unequal.
Texture: Pitted.
Ridges: On both sides of stone with ventral edge relatively narrow.
Tendency to split: None evident externally.
Use: Fresh Market; shipping variety for out-of-hand consumption by consumer from retail purchase.
Shipping and quality: Very Good.
Like most peach trees, the new variety has winter hardiness, and is not susceptible to damage during the dormant season. The fruit and foliage of the new variety do not evidence any particular susceptibility to heat.

The above description of this new variety of peach tree is based on the growing conditions prevailing near Sanger, Calif. in the Central San Joaquin Valley of California, variations of the usual magnitude and characteristics may occur due to change in cultural factors, including irrigation, fertilization, primary climatic changes, etc.

What is claimed is:

1. A new and distinct variety of peach tree as described and illustrated which is somewhat similar to 'Calara' (U.S. Plant Pat. No. 15,496), but from which it is distinguished by producing fruit that ripens weeks later than 'Calara', with good exterior coloration and very good eating quality which are mature for commercial harvesting and shipment approximately October 15-31 in a normal year.

* * * * *